United States Patent [19]
Morin

[11] Patent Number: 5,044,358
[45] Date of Patent: Sep. 3, 1991

[54] TREATMENT BENCH

[75] Inventor: Hans Morin, Akers Styckebruk, Sweden

[73] Assignee: Oy Suomen Selkapalvelu, Kristinestad, Finland

[21] Appl. No.: 461,757

[22] Filed: Jan. 8, 1990

[30] Foreign Application Priority Data

Jan. 13, 1989 [SE] Sweden ............................... 8900118

[51] Int. Cl.[5] .......................... A61F 5/00; A61F 5/04; A63B 23/02

[52] U.S. Cl. ....................................... 128/71; 128/74; 128/75; 272/144; 272/145

[58] Field of Search ....................... 272/144, 145, 903; 128/70-75, 845; 269/322, 323, 324, 328

[56] References Cited

U.S. PATENT DOCUMENTS

| | | | |
|---|---|---|---|
| 3,998,218 | 12/1976 | Cane et al. | 128/70 |
| 4,627,422 | 12/1986 | Bates | 128/71 |
| 4,726,358 | 2/1988 | Brady | 128/72 |
| 4,890,604 | 1/1990 | Nelson | 128/71 |

*Primary Examiner*—Richard J. Apley
*Assistant Examiner*—Karen G. Horowitz
*Attorney, Agent, or Firm*—Cushman, Darby & Cushman

[57] ABSTRACT

The treatment bench includes a stand which has mounted thereon a bench-section which can be swung relative to the stand about a horizontal pivot shaft. The pivotal bench-section carries a foot-rest at its one end and a patient-reclining surface substantially at its other end. The patient-reclining surface is connected by means of suspension links to a frame-part attached to the pivotal bench-section, and the suspension links are pivotally connected to the frame-part and to the reclining surface.

2 Claims, 3 Drawing Sheets

TREATMENT BENCH

BACKGROUND OF THE INVENTION

The present invention relates to a treatment bench of the kind which is intended particularly, but not exclusively, for the treatment of persons suffering from back ailments by so-called autotraction.

Treatment benches of this kind include a stand or frame structure which has mounted thereon a bench-section which can be swung relative to the stand about a pivot shaft which extends substantially horizontally to the stand. This pivotal bench-section carries a foot-rest at its one end and a patient-reclining surface at its other end. The pivotal bench-section can be swung about the horizontal shaft from an initial position in which the foot-rest faces essentially downwards and the patient-reclining surface faces upwards, to a position in which the head of a patient positioned on the bench is lower than the patient's feet and in which the foot-rest is located above the horizontal shaft and the patient-reclining surface is located beneath said shaft. The treatment bench may be adjustable solely to a position in which the patient hangs substantially vertically while supported by his feet.

In those instances when such a treatment bench is used solely to subject a patient lying on the patient-reclining surface to traction forces under the action of his own weight and the patient is thus not suspended by his feet, considerable friction will be generated between the patient's back and the patient-reclining surface, which counteracts stretching of the patient.

Treatment benches of this kind are known on which the patient-reclining surface has the form of a board which is mounted on wheels such as to enable the board to be displaced along a frame which forms part of the aforesaid pivotal bench-section and therewith, through the mobility of the board, enable the patient to be stretched, by transferrence of the frictional forces from the region between the patient's back and the board to a location between the board and the frame.

SUMMARY OF THE INVENTION

The object of the invention is to provide an improved treatment bench of the aforesaid kind in which the patient-reclining surface is configured in a manner more suitable for the treatment of such patients.

BRIEF DESCRIPTION OF THE DRAWINGS

The invention will now be described in more detail with reference to a non-limiting embodiment thereof illustrated in the accompanying drawings, in which.

DETAILED DESCRIPTION

Figure 1:
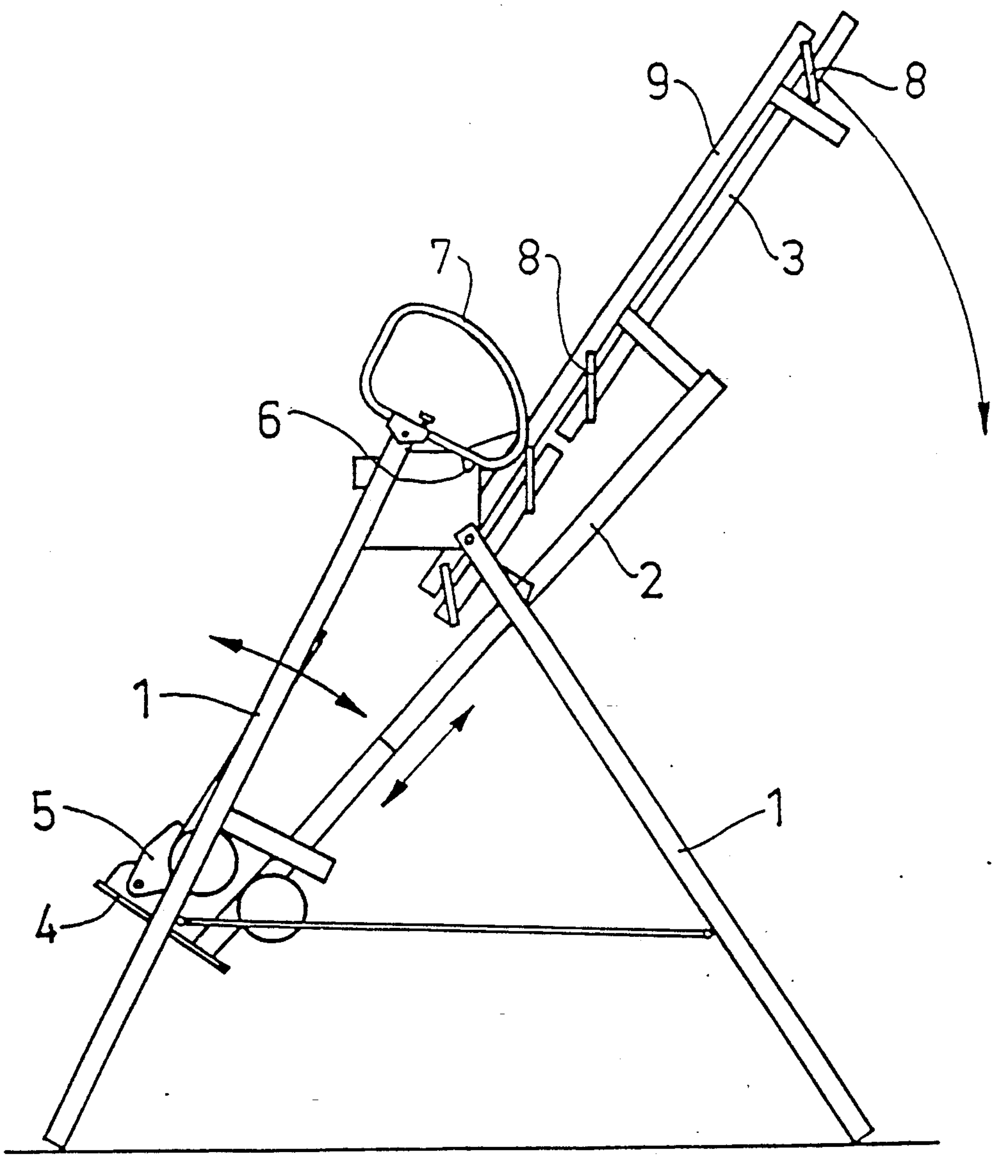
FIG. 1 illustrates schematically and in side view a treatment bench which is provided with a patient-reclining surface according to the invention.
Figure 2:
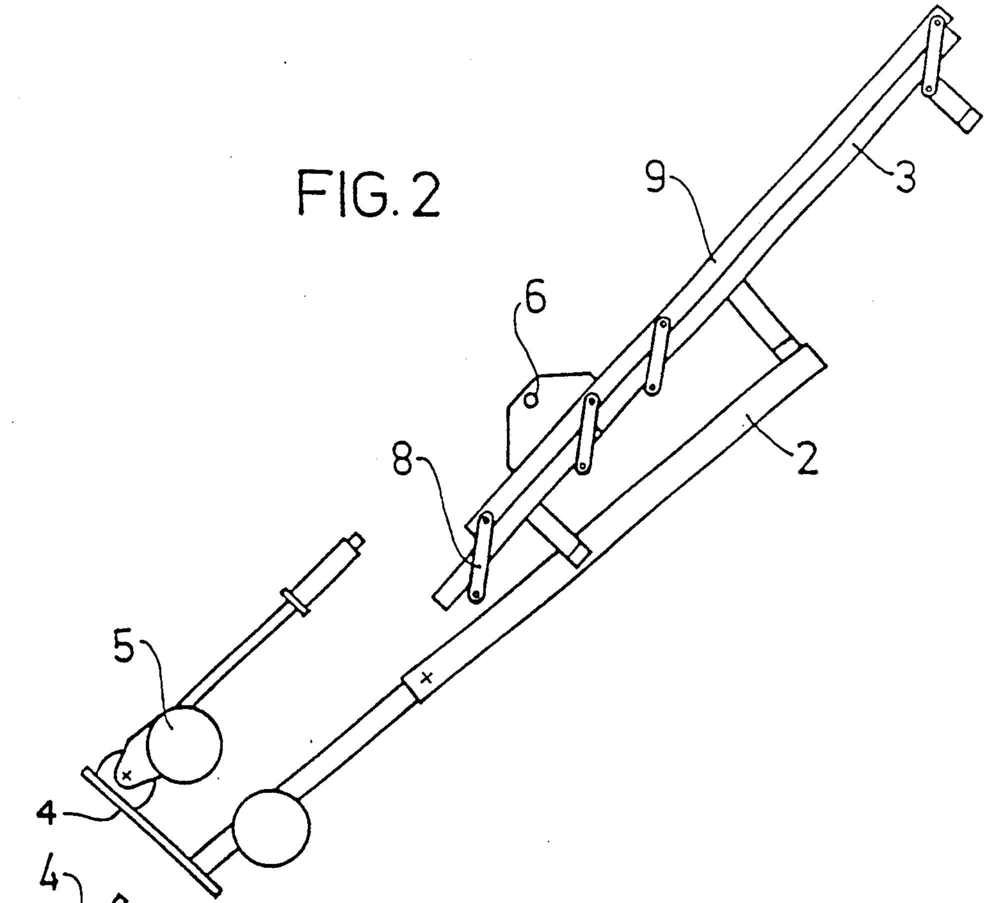
FIG. 2 illustrates schematically and in side view solely the pivotal section of the bench, with the pivotal bench-section shown in the same position as in FIG. 1.

There is illustrated in FIG. 1 a treatment bench which includes a stand 1 on which there is mounted for pivotal movement relative to the stand a section 2 which carries a patient-reclining surface 3 on one end thereof. Attached at the other end of the section 2 is a foot-rest 4 which coacts with a locking device 5 which functions to secure the feet of a person lying on the surface 3. The bench-section 2, and therewith also the surface 3, can be pivoted about a substantially horizontal pivot axis on shafts 6, so as to swing the foot-rest 4 from the head up-feet down inclined position shown in FIGS. 1 and 2 to a head down-feet up inclined position, e.g. the position shown in FIG. 3, in which the patient lies with his feet pointing upwards and held securely by the locking device 5, so that the patient's spine will be stretched in an appropriate manner.

Figure 3:
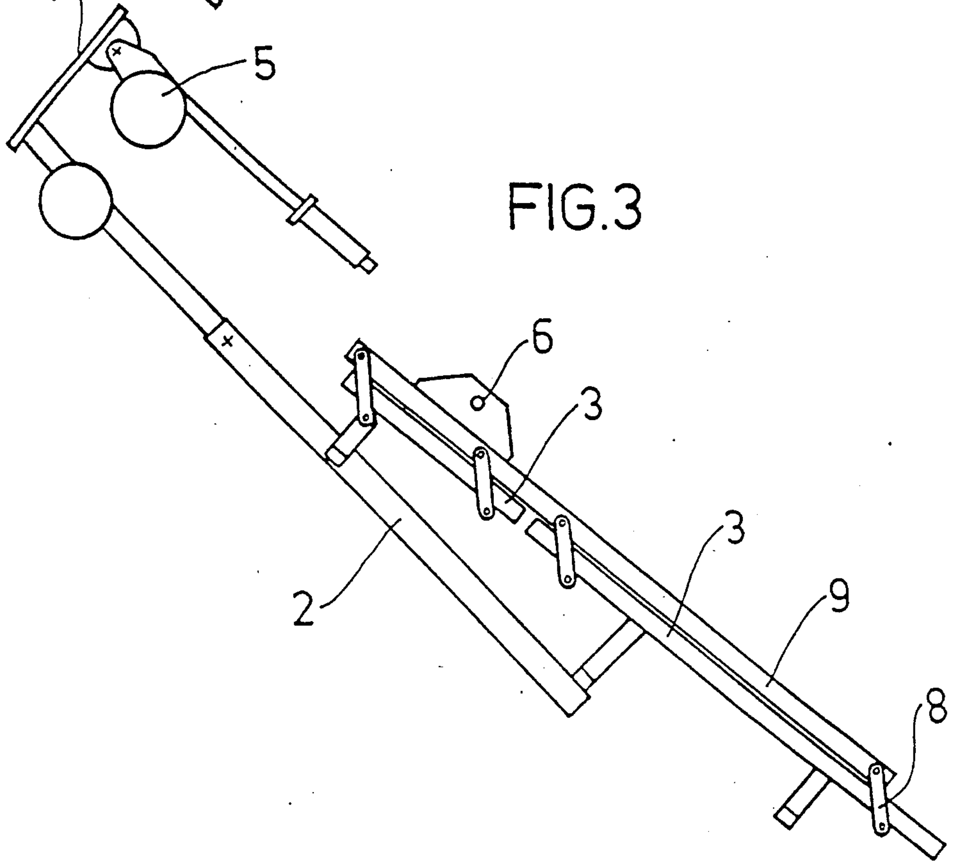
FIG. 3 illustrates schematically and in side view the pivotal section subsequent to being swung to a position in which the patient-reclining surface is located beneath the foot-rest.
Figure 4:
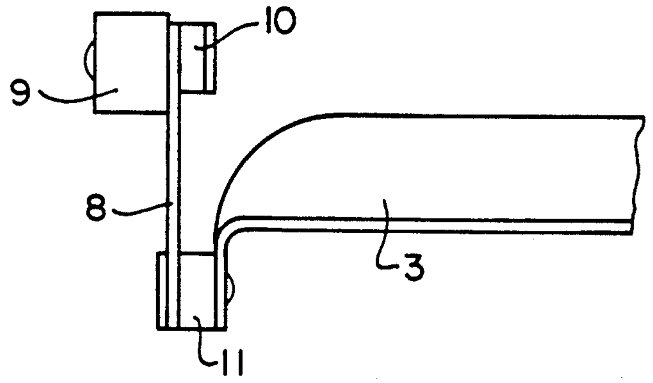
FIG. 4 is a fragmentary larger scale elevation view showing the suspension of the left side of the patient support member with its patient-reclining surface, from the left element of the frame-part, the non-shown right side of the bench being a mirror image of what is shown in FIG. 4.

In accordance with the invention, the patient-reclining surface 3 is attached by means of suspension links 8 to a frame-part 9 which is mounted rigidly on the pivotal bench-section 2. The patient-reclining surface 3 may consist of a single board or slab which is connected to the frame-part 9 by means of the suspension links 8, or may alternatively comprise a plurality of sections, as shown in FIG. 3, where each section is connected to the frame-part 9 by respective suspension links 8.

The suspension links are pivotally connected at their upper ends to the frame-part 9 at both sides by a plurality of first, upper pivot joints 10, and are pivotally connected at their lower ends to the patient-reclining surface 3 at both sides by a plurality of second, lower pivot joints 11. The lower pivot joints 11 are located below the patient-reclining surface 3. Because the suspension links are pivotally mounted, the links will constantly strive to take a substantially vertical position and consequently the links will be effective in displacing the patient-reclining surface 3 in relation to the frame-part 9, when the pivotal bench-section is swung about the horizontal shafts 6, e.g., from the position shown in FIG. 2 to the position shown in FIG. 3. When there is no one is on the reclining surface 3, the surface will be displaced readily such that the links 8 will always take a substantially vertical position when the pivotal bench-section is swung around the shafts 6.

When a person positions himself or herself so that his or her feet rest on the foot-rest 4 and secures his or her feet by means of the locking device 5 and releases a brake mechanism 7, the person is able to swing the pivotal bench-section about the horizontal shafts 6, so that he or she lies substantially upside down on the bench. The person can adjust his or her position as desired, by means of the brake mechanism. Because the suspension links 8 are pivotally connected to the frame-part 9, the patient-reclining surface 3 will also be displaced relative to frame-part 9 with a patient resting on said surface, when the pivotal bench-section 2 is rotated about the horizontal shaft 6, such that the spine of the patient will be placed in traction, due to the fact that the reclining surface 3 strives to increase the distance from the foot-rest 4, although in this case the links 8 will not be able to adopt a fully vertical position, because of the weight exerted by the person resting on the surface 3. On the other hand, the spine of the person resting on the reclining surface 3 will be stretched to the maximum possible extent, i.e. to the same extent as when the person concerned is suspended solely by his or her feet, although in this case the person rests on the reclining surface 3.

As before mentioned, the patient-reclining surface 3 may comprise a plurality of sections, each being pivotally journalled to the frame-part 9 by respective suspension links 8, in the aforedescribed manner. These sections may have mutually different configurations, so as to afford the best support for the body of the person lying on the surface 3. For instance, the sections may be configured particularly to support the lumbar region and hind-quarters of the person lying on the reclining surface.

I claim:

1. A treatment bench for suspending a head down, feet up incliningly reclining patient from his or her feet with his or her back thereby subjected to traction, comprising:

a stand;

a bench-section having two longitudinally opposite ends and two laterally opposite sides;

means pivotally securing said bench-section to said stand for pivotal motion about a first transverse horizontal axis between a first position in which one said end of said bench-section is higher than the other said end of said bench-section, and a second position in which said one end of said bench-section is lower than said other end of said bench-section;

means providing a foot-rest on said bench-section at said other end thereof;

means defining a longitudinally extending frame-part secured to said bench-section at said one end thereof;

at least one patient support member having a patient-reclining surface means provided thereon at a location that is spaced longitudinally along said bench-section from said foot rest;

a plurality of generally vertically extending suspension links each having one end pivotally secured to said frame-part for pivoting about a respective transverse, horizontal axis pivot axis, and another end pivotally secured to a respective said patient support member for pivoting about a respective transverse, horizontal axis pivot axis, so that a patient may board said bench while said bench-section is located in said first position, secure his or her feet to said foot rest and support his or her torso on said patient-reclining surface means, and said bench-section may then be pivoted relative to said stand about said first horizontal axis, to said second position, whereby said suspension links pivot to tend to remain generally vertical, causing the relative distance between the foot-rest and the patient support member to increase and, consequently, the patient's torso to become stretched axially away from the patient's feet;

said frame-part comprising left and right elements disposed above each said patient support member, with said suspension links hangingly supporting each said patient support member from said left and right elements of said frame-part.

2. The treatment bench of claim 1, wherein:

said at least one patient support member is constituted by at least two patient support members spaced longitudinally from one another relative to said bench-section, so that said suspension members can permit longitudinal movement of said patient support members relative to one another as said bench section is pivoted from said first position to said second position.

* * * * *